United States Patent [19]

Sharifian et al.

[11] Patent Number: 4,938,854
[45] Date of Patent: Jul. 3, 1990

[54] METHOD FOR PURIFYING QUATERNARY AMMONIUM HYDROXIDES

[75] Inventors: Hossein Sharifian; Alan R. Tanner, both of Austin, Tex.

[73] Assignee: Southwestern Analytical Chemicals, Inc., Austin, Tex.

[21] Appl. No.: 276,615

[22] Filed: Nov. 28, 1988

[51] Int. Cl.$^5$ ............................................. C25F 1/00
[52] U.S. Cl. .................................. 204/130; 204/128; 204/250; 204/251; 204/252; 204/292; 204/293
[58] Field of Search ........... 204/128, 72, 130, 250-252, 204/292, 293

[56] References Cited

U.S. PATENT DOCUMENTS

| | | | |
|---|---|---|---|
| 3,523,068 | 8/1970 | Eisenhauer et al. | 204/72 |
| 4,394,226 | 7/1983 | Wade et al. | 204/72 |
| 4,425,202 | 1/1984 | Sullivan | 204/72 |
| 4,521,285 | 6/1985 | De Witt et al. | 204/72 |
| 4,572,769 | 2/1986 | Shimigi | 204/59 R |
| 4,578,161 | 3/1986 | Buonomo et al. | 204/128 |
| 4,714,530 | 12/1987 | Hale et al. | 204/131 |

FOREIGN PATENT DOCUMENTS

| | | |
|---|---|---|
| 155390 | 9/1982 | Japan . |
| 100690 | 6/1985 | Japan . |
| 131985 | 7/1985 | Japan . |
| 131986 | 7/1985 | Japan . |

OTHER PUBLICATIONS

Chemical Abstracts, vol. 103, No. 20, Nov. 1985, p. 556, Abstract No. 168739s and JP, A, 60131985.
Chemical Abstracts, vol. 107, No. 26, Dec. 1987, p. 556, Abstract No. 245184u and JP, A, 62139890.
Chemical Abstracts, vol. 102, No. 8, Feb. 1985, pp. 476-477, Abstract No. 69382t and JP, A 59193289.

Primary Examiner—John F. Niebling
Assistant Examiner—Kathryn Gorgos
Attorney, Agent, or Firm—Renner, Otto, Boisselle & Sklar

[57] ABSTRACT

A process for treating solutions of quaternary ammonium hydroxide containing latent halide to lower the latent halide content of the solution comprises the steps of (A) providing an electrolytic cell comprising an anode and a cathode wherein the cathode comprises zinc, cadmium, tin, lead, copper or titanium or alloys thereof, mercury or mercury amalgam, (B) charging a solution containing at least one quaternary ammonium hydroxide which contains latent halide into the electrolytic cell, (C) passing a current through the electrolytic cell to lower the latent halide content in the solution, and (D) recoverying the quaternary ammonium hydroxide solution from the electrolytic cell.

36 Claims, 1 Drawing Sheet 4,938,854

METHOD FOR PURIFYING QUATERNARY AMMONIUM HYDROXIDES

TECHNICAL FIELD

This invention relates to a method of improving the purity of quaternary ammonium hydroxides. The invention also relates to the high purity quaternary ammonium hydroxides obtained by the method of the invention.

BACKGROUND OF THE INVENTION

Quaternary ammonium hydroxide such as tetramethyl ammonium hydroxide (TMAH) and tetraethyl ammonium hydroxide (TEAH) are strong organic bases that have been known for many years. Such quaternary ammonium hydroxides have found a variety of uses including use as a titrant for acids in organic solvents and as a supporting electrolyte in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium and potassium, and halides such as chlorine, bromine, iodine, etc. Particularly in recent years, there has been an increasing demand for quaternary ammonium hydroxides having a high purity.

Quaternary ammonium hydroxides such as TMAH and TEAH have been produced by various techniques. Generally, the quaternary ammonium hydroxides are manufactured by electrolyzing a salt of a quaternary ammonium compound in an electrolysis cell containing a diaphragm formed of a cation-exchange membrane. The quaternary ammonium salts used in such preparations include halide salts, carboxylate salts, carbonate salts and sulfate salts. When halide salts are used in the manufacture of quaternary ammonium hydroxide, it has been discovered that the quaternary ammonium hydroxide solutions formed by this method generally contain significant amounts of halogen (ionic and latent), generally in concentrations from about 30 ppm up to about 100 ppm at 25% quaternary ammonium hydroxide (e.g., TMAH). The term "latent halide" is used throughout this specification and claims to refer to nonionic halogen which is present in the aqueous quaternary ammonium hydroxide solutions, and which is capable of forming halide ions under certain conditions such as heating.

Among the prior art patents which describe the preparation of quaternary ammonium hydroxides by electrolyzing a salt of a quaternary ammonium compound are U.S. Pat. Nos. 4,572,769; 4,521,285; 4,425,202; and 4,394,226. U.S. Pat. No. 4,572,769 describes the use of formate salts to form the quaternary ammonium hydroxides, and this patent suggests that some of the problems of using quaternary ammonium halides are minimized by use of the formate salt. The formate salts are prepared by the reaction of a trialkyl amine with methyl forxate in either methanol or ethanol as solvent. U.S. Pat. No. 4,521,285 describes an electrolyte process for removing the anion from quaternary organic salts. The process uses a cell comprising four compartments containing two cation exchange membranes and one anion exchange membrane. U.S. Pat. No. 4,425,202 describes a process for making choline base by electrolysis of choline chloride in an electrolytic cell. Color stabilization of choline base is effected through concentration control and/or the addition of a sulfite prior to electrolytic manufacture of the choline base. U.S. Pat. No. 4,394,226 describes production of quaternary ammonium hydroxides in electrolytic cells using cationic membranes which have been treated with a mineral acid prior to use in the electrolysis.

U.S. Pat. No. 4,714,530 describes an electrolytic process for preparing high purity quaternary ammonium hydroxides which utilizes a cell containing a catholyte compartment and an anolyte compartment separated by a cation-exchange membrane. The process comprises charging an aqueous solution of a quaternary ammonium hydroxide to the anolyte compartment, adding water to the catholyte compartment, and passing a direct current through the electrolysis cell to produce a higher purity quaternary ammonium hydroxide in the catholyte compartment which is subsequently recovered. The '530 patent also describes an improvement which comprises heating the quaternary ammonium hydroxide at an elevated temperature prior to charging the hydroxide to the anolyte compartment of the electrolytic cell.

SUMMARY OF THE INVENTION

A process is described for reducing the latent halide content of a solution of quaternary ammonium hydroxide containing latent halide which comprises the steps of (A) providing an electrolytic cell comprising an anode and a cathode, (B) charging a solution containing at least one quaternary ammonium hydroxide which contains latent halide into said electrolytic cell, (C) passing a current through the electrolytic cell to lower the latent halide content in the solution, and (D) recovering the quaternary ammonium hydroxide solution from the electrolytic cell.

A process also is described for reducing the latent halide content of quaternary ammonium hydroxides prepared from the corresponding halide which comprises (A) providing an electrolytic cell comprising an anolyte compartment containing an anode and a catholyte compartment containing a cathode separated by a divider, (B) charging a solution containing said quaternary ammorium hydroxide which contains latent halide into the catholyte compartment, (C) charging an electrolyte to the anolyte compartment, (D) passing a current through the electrolytic cell to lower the latent halide content of the solution in the catholyte compartment, and (E) recovering the quaternary ammonium hydroxide solution from the catholyte compartment.

DESCRIPTION OF THE PREFERRED EMBODIMENTS

Figure 1:
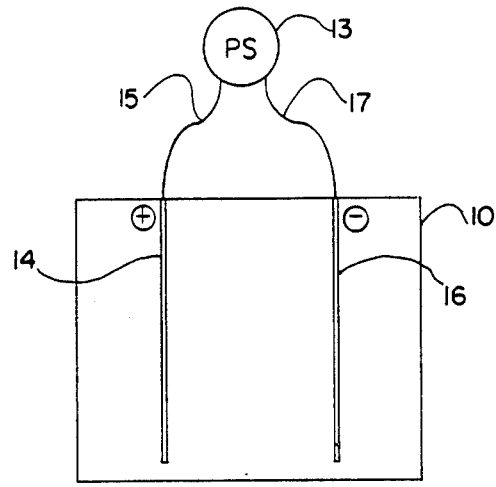
FIG. 1 is a schematic cross-section of an electrolytic cell useful in performing the process of the invention.

The quaternary ammonium hydroxide solutions which are treated in accordance with the process of the present invention to improve the purity thereof generally are aqueous solutions containing quaternary ammonium hydroxides characterized by the formula

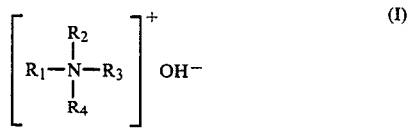

wherein $R_1$, $R_2$, $R_3$ and $R_4$ are each independently alkyl groups containing from one to about 10 carbon atoms, hydroxyalkyl groups containing from two to atout 10 carbon atoms, alkoxyalkyl groups containing from two to about 10 carbon atoms, aryl groups, or hydroxyaryl groups.

Specific examples of alkyl groups containing from one to 10 carbon atoms include methyl, ethyl, proyl, butyl, pentyl, hexyl, heptyl, octyl, nonyl, and decyl groups. $R_1$, $R_2$, $R_3$ and $R_4$ also may be hydroxyalkyl groups such as hydroxyethyl and the various isomers of hydroxypropyl, hydroxybutyl, hydroxypentyl, etc. Specific examples of alkoxyalkyl groups include ethoxyethyl, butoxyethyl, butoxybutyl, etc. Examples of various aryl and hydroxyaryl groups include phenyl, benzyl, and equivalent groups wherein benzene rings have been substituted with one or more hydroxy groups.

Examples of quaternary ammonium hydroxides which can be treated in accordance with the process of the present invention include tetramethylammonium hydroxide, tetraethylammonium hydroxide, tetrapropylammonium hydroxide, trimethylhydroxyethylammonium hydroxide, dimethyldihydroxyethylammonium hydroxide, methyltrihydroxyethylammonium hydroxide, phenyltrimethylammonium hydroxide, phenyltriethylammonium hydroxide, benzyltrimethylammonium hydroxide, etc.

In one preferred embodiment, the R groups are alkyl groups containing from one to three carbon atoms and hydroxy alkyl groups containing two or three carbon atoms. Most often, the quaternary ammonium hydroxides treated in accordance with the process of the present invention will be tetramethylammonium hydroxide (TMAH) or tetraethylammonium hydroxide (TEAH).

The aqueous solutions of quaternary ammonium hydroxides which can be treated in accordance with the process of the present invention may be prepared by any of the known techniques. Generally, the quaternary ammonium hydroxides which are purified in accordance with the process of the present invention are quaterrary ammonium hydroxides manufactured by electrolyzing quaternary ammonium salts, particularly a quaternary ammonium halide, in an electrolysis cell containing a diaphragm formed of a cation-exchange membrane. Procedures such as described in U.S. Pat. No. 4,394,226 and in other publications for the electrolysis of quaternary ammonium halides generally constitute the source of the quaternary ammonium hydroxides purified in accordance with the process of the present invention.

The quaternary ammonium hydroxides which are purified in accordance with the process of the present invention are aqueous solutions containing from about 3 to about 55% by weight or about 3 to about 50% by weight of the hydroxide and generally will contain significant amounts of halogen. For example, aqueous solutions of quaternary ammonium hydroxides prepared by the electrolysis of quaternary ammonium halides typically may contain, at 25% w of quaternary ammonium hydroxide, from about 15 to about 200 ppm of ionic halide and from about 5 to about 75 ppm of latent halide. Unless otherwise specifically indicated in this application all references to, and analytical results relating to ppm of halide, metals, or carbonates are for aqueous solutions containing 25% w of the quaternary ammonium hydroxide.

In one embodiment, the process of the present invention is effective in reducing the amount of latent halide present in the quaternary ammonium hydroxides. In this embodiment, the latent halide is converted to ionic halide. In another embodiment, the process of the present invention results in the reduction in the concentration of ionic halide present in quaternary ammonium hydroxides, and in yet a further embodiment, the process of the present invention results in a reduction of both latent and ionic halide in a quaternary ammonium hydroxide subjected to the process of the present invention.

In one embodiment, the latent halide content of a solution of quaternary ammonium hydroxide is reduced by the process which comprises the steps of (A) providing an electrolytic cell comprising an anode and a cathode, (B) charging a solution containing at least one quaternary ammonium hydroxide which contains latent halide into said electrolytic cell, (C) passing a current through the electrolytic cell to lower the latent halide content in the solution, and (D) recovering the quaternary ammonium hydroxide solution from the electrolytic cell. A schematic cross-section or representation of an electrolytic cell which can be utilized to carry out the above process of the present invention is shown in FIG. 1. In this figure, the electrolytic cell 10 comprises an anode 14 and the cathode 16. The anode 14 is attached to power supply 13 by wire 15, and the cathode 16 is attached to power supply 13 through wire 17.

Various materials which have been used as anodes in electrolytic cells can be included in the cells used in the above and other embodiments of the present invention provided they do not react with the solution added to the cells. For example, the anode may be made of high purity graphite or metals such as, for example, titanium-coated or clad electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

Various materials which have been used as cathodes in electrolytic cells can be included in the cells used in the above and other embodiments of the present invention. Cathode materials include nickel, iron, stainless steel, nickel plated titanium, etc. Preferably, the cathodes in electrolytic cells utilized in the process of the present invention comprise zinc, cadmium, tin, lead, copper, iron or titanium or alloys thereof, mercury or mercury amalgams. The term "alloy" is used in a broad sense and includes intimate mixtures of two or more metals as well as one metal coated onto another metal. The mercury amalgam cathodes include, for example, mercury on nickel, mercury on copper, mercury on cadmium, mercury on zinc, etc. It has been discovered that these preferred cathode materials are particularly effective in reducing the amount of latent halide contained in the quaternary ammonium hydroxides.

The concentration of quaternary ammonium hydroxide in the aqueous solution charged to the electrolytic cell in accordance with the above process generally will be from about 3 to about 55% by weight. More generally, the concentration will be from about 5 to about 30% by weight. During the electrolysis, it is desirable that the temperature of the liquid within the cell be maintained within the range of from about 10° to about 70° C., and more generally, the temperature is maintained at about 50° C. or below during electrolysis.

Electrolysis of the aqueous solution containing the quaternary ammonium hydroxide contained in the electrolytic cell is effected by impressing a current voltage (generally direct current) between the anode and the cathode with a current density of about 5 to about 250 A/ft$^2$, and more preferably at a current density of from about 25 to about 150 A/ft$^2$. Alternatively, the current density may be about 1–100 A/dm$^2$ or 10–50 A/dm$^2$. The current density is applied to the cell for a period of time which is sufficient to result in the desired reduction in latent halide content in the quaternary ammonium hydroxide solution. Circulation is effected by pumping and/or by gas evolution. In practice, such an electrolytic cell can be operated batchwise or in a continuous operation.

In another embodiment, the process of the present invention is carried out in an electrolytic cell which comprises an anolyte compartment containing an anode and a catholyte compartment containing a cathode, the two compartments being separated by a gas separating divider. More specifically, the process of this embodiment comprises the steps of (A) providing an electrolytic cell comprising an anolyte compartment containing an anode and a catholyte compartment containing a cathode separated by a divider, (B) charging a solution containing said quaternary ammonium hydroxide which contains latent halide into the catholyte compartment, (C) charging an electrolyte to the anolyte compartment, (D) passing a current through the electrolytic cell to lower the latent halide content of the solution in the catholyte compartment, and (E) recovering the quaternary ammonium hydroxide solution from the catholyte compartment.

The divider in the above-described electrolytic cell may be any material which functions as a gas separator. Examples of such divider materials include inert fabrics, sintered glass, ceramics, and membrane diaphragms. Membrane diaphragms are particularly useful and are preferred. The membrane dividers may be either anion-exchange membranes or cation-exchange membranes.

Figure 2:
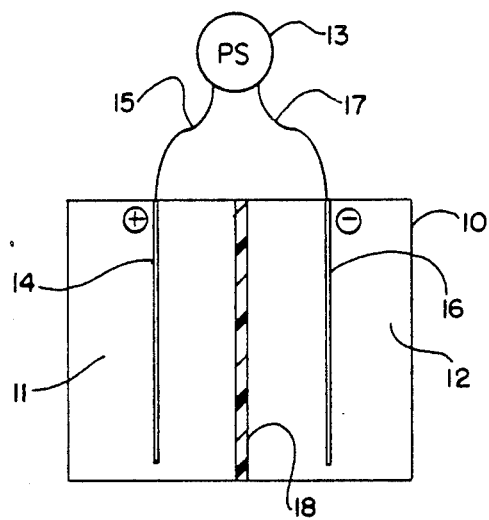
FIG. 2 is a schematic cross-section of a preferred electrolytic cell useful in performing the process of the invention.

A schematic cross-sectional representation of an electrolytic cell for carrying out the process of this embodiment and utilizing a divider such as a membrane diaphragm is shown in FIG. 2. In this figure, the electrolytic cell 10 comprises an anolyte compartment 11 and a catholyte compartment 12 separated from each other by membrane 18. The anolyte compartment 11 contains anode 14 which is attached to power supply 13 by wire 15. The catholyte compartment 12 contains cathode 16 which is attached to power supply 13 through wire 11.

The materials identified previously as being useful as anodes and cathodes can be utilized as the anodes and cathodes in this embodiment, and, as in the previous embodiment, the cathodes preferably comprise zinc, cadmium, tin, lead, copper, iron or titanium or alloys thereof, mercury or mercury amalgam. The process of the present invention utilizing an electrolytic cell of the type described above and shown in FIG. 2 is illustrated by the following representative example. An aqueous solution containing a quaternary ammonium hydroxide is charged to the catholyte compartment 12, and an electrolyte is charged to the anolyte compartment 11. An electrical potential is established and maintained by power source 13 between anode 14 and cathode 16 to produce a flow of current across the cell 10 to convert latent halide to halide ions. The quaternary ammonium hydroxide solution may be removed from the catholyte compartment when the latent halide content has been reduced to the desired extent.

The electrolyte charged to the anolyte compartment may be any aqueous or non-aqueous liquid capable of conducting electricity such as, for example, a methanol solution of a quaternary ammonium hydroxide, aqueous sodium chloride, aqueous sodium hydroxide, aqueous quaternary ammonium hydroxides, etc. Aqueous sodium hydroxide solutions and aqueous solutions of quaternary ammonium hydroxides are particularly useful as electrolytes in the anolyte compartment.

As noted previously, the electrolysis cell utilized in the process of the present invention may contain ion-exchange membranes as dividers. The ion-exchange membranes may be either cation-exchange membranes or anion exchange membranes. These membranes belong to the well-known classes of organic commercial polymers containing polar groups of anionic or cationic character in the form of thin films. The membranes are capable of transferring either anions or cations, i.e., they are permeable to certain kinds of ions but substantially less permeable or even impermeable to others. The preparation and structure of anionic and cationic membranes are described in the chapter entitled "Membrane Technology" in *Encyclopedia of Chemical Technology*, Kirk-Othmer, Third Edition, Volume 15, pp. 92–131. Wiley & Sons, N.Y., 1985. These pages are hereby incorporated by reference for their disclosure of various anionic and cationic membranes which can be useful in the process of the present invention.

The cation-exchange membrane may be any of those which have been used in the electrolysis of quaternary ammonium salts to quaternary ammonium hydroxides. Preferably, the cation-exchange membranes should comprise a highly durable material such as the membranes based on the fluorocarbon series, or from less expensive materials of the polystyrene or polypropylene series. Preferably, however, the cationic membranes useful in the present invention include fluorinated membranes containing cation exchange groups such as perfluorosulfonic acid and perfluorosulfonic acid/perfluorocarboxylic acid perfluorocarbon polymer membranes such as sold by the E. I. duPont de Nemours & Company under the trade designation "NAFION". Other suitable cation-exchange membranes include styrene-divinylbenzene copolymer membranes containing cation-exchange groups such as sulfonate groups, carboxylate groups, etc.

Among the anionic membranes which can be utilized and which are commercially available are the following: AMFLON Series 310, based on fluorinated polymer substituted with quaternary ammonium, produced by American Machine and Foundry Company, and Ionac MA 3148, MA 3236 and MA 3475, based on polymer substituted with quaternary ammonium derived from heterogeneous polyvinyl chloride produced by Ritter-Pfaulder Corp., Permutit Division, etc.

In the above embodiments, when the membrane is a cationic membrane and the quaternary ammonium hydroxide solution containing latent halide is charged to the catholyte compartment, the process results in the recovery of the quaternary ammonium hydroxide containing significantly reduced amounts of latent halide and a correspondingly increased amount of ionic halide which can then be removed by procedures such as described in U.S. Pat. No. 4,714,530 or as described below.

Alternatively, the electrolytic cell utilized in the process of the present invention and illustrated in FIG. 2 can be prepared utilizing an anion-exchange resin. When this electrolytic cell is employed are a solution of quaternary ammonium hydroxide containing latent halide and ionic halide is charged to the catholyte compartment, and a direct current is passed through the electrolytic cell in a manner described with regard to the other embodiments described above, a one- or two-step process occurs depending upon the conditions employed including time. Initially, when a current is passed through the electrolytic cell containing the anion-exchange membrane, the concentration of latent halogen contained in the catholyte is reduced with a corresponding increase in ionic halide. As the process continues and the current continues to pass through the cell, the ionic halide in the solution contained in the catholyte migrates from the catholyte compartment to the anolyte compartment through the anion-exchange membrane where chloride ions are converted to chlorine gas at the anode, and the chlorine gas is collected and removed by gas-collecting means (not shown). The quaternary ammonium hydroxide recovered from the catholyte thus will contain substantially no detectable latent halide and a lesser amount of ionic halide than a similar process using an electrolysis cell having a cation-exchange membrane.

Electrolysis of the solutions containing the quaternary ammonium hydroxide, latent halogen and ionic halide in the electrolytic cells containing dividers such as ion-exchange membranes is effected by impressing a current voltage (generally direct current voltage) between the anode and cathode with a current density of from about 5 to about 250 A/ft$^2$, and more preferably the current density of from about 25 to about 150 A/ft$^2$. Alternatively, the current density may be from about 1 to about 100 A/dm$^2$ or 10-50 A/dm$^2$. The current is applied to the cell for a period which is sufficient to result in the desired reduction of latent halogen or reduction in both latent halogen and ionic halide in the solutions contained in the catholyte compartment. Circulation is effected by pumping and/or by gas evolution, and, in practice, the electrolytic cell can be operated batchwise or in a continuous operation.

Aqueous solutions of quaternary ammonium hydroxide purified and recovered in accordance with the processes of the present invention generally will contain from zero to 5 ppm of latent halogen and varying amounts of ionic halide depending upon the particular embodiment utilized and the period of time the process is conducted. For example, as mentioned above, when an anionexchange resin is utilized and the process is conducted for an extended period, the ionic halide content of the recovered quaternary ammonium hydroxide can be reduced significantly.

The following examples illustrate the processes of the present invention. Unless otherwise indicated in the following examples and elsewhere in the specification and claims, all parts and percentages are by weight, all temperatures are in degrees centigrade, and pressure is at or near atmospheric pressure.

EXAMPLE 1

An electrolytic cell is prepared utilizing a 15 ml. beaker equipped with a mercury pool cathode, platinum auxiliary electrode, and a saturated calomel reference electrode (SCE). The electrolyte solution charged to the beaker is 10 ml. of 25% tetramethyl ammonium hydroxide which contains about 50 ppm. latent chloride. The electrolysis is carried out at a constant potential of $-2.40$ volts, and the cell current is about 5.0 mA. Analysis of the electrolyte solution after one hour indicates no detectable latent chloride.

EXAMPLE 2

An electrolytic cell is prepared cadmium cathode and a platinum clad tantalum anode. The anolyte and catholyte compartments are separated by means of a NAFION 901 membrane (DuPont). The anolyte compartment is filled with 100 ml. of pure 25% tetramethylammonium hydroxide aqueous solution, and the catholyte compartment is filled with 12% aqueous solution of tetramethylammonium hydroxide containing 50 ppm. of latent chloride. Electrolysis is carried out at a current density of about 75 A/Ft$^2$ at a temperature of about 50° C. for a period of about one hour. Analysis of the catholyte solution upon completion of the electrolysis reveals essentially no detectable latent chloride.

EXAMPLE 3

The general procedure of Example 2 is repeated except that the cell is equipped with a lead cathode. At the end of one hour, analysis of the catholyte solution indicated no detectable latent chloride.

EXAMPLE 4

The general procedure of Example 2 is repeated utilizing an amalgamated copper cathode. Analysis of the catholyte solution after one hour indicates that the solution contains no detectable latent chloride.

EXAMPLE 5

The general procedure of Example 2 is repeated except that the cathode is an amalgamated nickel cathode. Analysis of the catholyte solution after one hour of electrolysis indicates the solution contains no detectable latent chloride.

EXAMPLE 6

The electrolytic cell utilized in this example is an open two-compartment cell equipped with a zinc cathode, a platinum clad tantalum anode and a NAFION 425 cation permeable membrane. The cathode compartment is charged with 25 ml. of 25% aqueous tetramethylammonium hydroxide containing 23.0 ppm. of ionic chloride and a quantity of latent chloride (about 20-30 ppm.). The anode compartment is charged with 25 ml. of 4M sodium hydroxide containing less than 0.04 ppm. ionic chloride. Approximately 22 cm$^2$ of each electrode is immersed in liquid, and a constant voltage (open voltage 8.4 vD.C.) is applied. A maximum cell current of about 6 amps is observed during the electrolysis. As the electrolysis proceeds, samples of the catholyte are taken and analyzed. Analysis indicates the following:

| Run No. | Minutes | Ionic Chloride, ppm |
|---|---|---|
| 1 | 0.0 | 23.0 |
| 2 | 5.0 | 30.4 |
| 3 | 15.0 | 41.1 |
| 4 | 30.0 | 47.2 |
| 5 | 45.5 | 47.0 |

The increase in ionic chloride is evidence that the latent chloride content of the solution is reduced. Ionic chloride concentration is determined by potentiometric silver titration using silver nitrate.

EXAMPLE 7

The electrolysis cell described in Example 6 is utilized at a constant current of 3.0 amps (about 75 A/ft$^2$). The catholyte is 25 ml. of a 25% aqueous tetramethylammonium hydroxide solution containing about 23.0 ppm. chloride ion and about 20–30 ppm. of latent chloride. The anolyte is 15 ml. of 4M sodium hydroxide containing less than 0.04 ppm. of chloride ion. The electrolysis is conducted for 30 minutes, and at the end of this period, analysis of the electrolyzed catholyte indicates an ionic chloride content of 44.5 (repeat 44.0).

EXAMPLE 8

The electrolysis cell utilized in this example is an open two-compartment cell equipped with a zinc cathode, a platinum clad tantalum anode, and an anion permeable membrane (RAl 5030). The cathode compartment is charged with 25 ml. of a 25% aqueous solution of tetramethylammonium hydroxide containing 22.7 ppm. ionic chloride and about 20 to 30 parts of latent chloride. The anode compartment is charged with 5.0 ml. of 4M sodium hydroxide containing less than 0.04 ppm. of chloride ion and 20 ml. of deionized water. Approximately 22 cm$^2$ of each electrode is immersed in the liquid. A constant voltage (open voltage −8.4 v D.C.) is applied and a maximum current of 6 amps is observed during the electrolysis. Analysis of the electrolyzed catholyte, as can be seen from the following table, shows an initial increase in the chloride ion content as the latent chloride is converted to ionic chloride followed by a decrease in the chloride ion content after one hour when the latent chloride has been converted to ionic chloride.

| Run No. | Minutes | Ionic Chloride, ppm |
|---|---|---|
| 1 | 0.0 | 22.7 |
| 2 | 5.0 | 31.0 |
| 3 | 15.0 | 44.5 |
| 4 | 30.0 | 48.8 |
| 5 | 45.0 | 45.8 |
| 6 | 60.0 | 42.0 |
| 7 | 120.0 | 25.2 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for the electrolysis of a solution of quaternary ammonium hydroxide containing latent halide to reduce the latent halide content therein which comprises the steps of
   (A) providing an undivided electrolytic cell comprising an anode and a cathode, wherein the cathode comprises zinc, cadmium, tin, lead, copper or titanium or alloys thereof, mercury or mercury amalgam.
   (B) charging a solution containing at least one quaternary ammonium hydroxide which contains latent halide into said electrolytic cell,
   (C) passing a current through the electrolytic cell to lower the latent halide content in the solution, and
   (D) recovering the quaternary ammonium hydroxide solution from the electrolytic cell.

2. The process of claim 1 wherein the quaternary ammonium hydroxide charged to the cell in step (B) is characterized by the formula

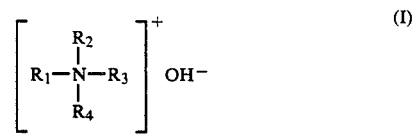

wherein $R_1$, $R_2$, $R_3$ and $R_4$ are each independently alkyl groups containing from one to about 10 carbon atoms, hydroxyalkyl or alkoxyalkyl groups containing from two to about 10 carbon atoms, aryl groups, or hydroxyaryl groups.

3. The process of claim 2 wherein $R_1$, $R_2$, $R_3$ and $R_4$ are each independently alkyl groups containing one to three carbon atoms or hydroxyalkyl groups containing two or three carbon atoms.

4. The process of claim 2 wherein $R_1$, $R_2$, $R_3$ and $R_4$ are methyl or ethyl groups.

5. The process of claim 1 wherein the quaternary ammonium hydroxide solution charged to the cell in step (B) also contains ionic chloride.

6. The process of claim 1 wherein the quaternary ammonium hydroxide solution containing latent halide is derived from the electrolysis of a quaternary ammonium halide salt in an electrolytic cell.

7. The quaternary ammonium hydroxide solution obtained by the process of claim 1.

8. The process of claim 1 wherein the cathode is a zinc or a zinc-alloy cathode.

9. A process for the electrolysis of a solution of quaternary ammonium hydroxide containing latent halide to reduce the latent halide therein which comprises the steps of
   (A) providing an electrolytic cell comprising an anolyte compartment containing an anode and a catholyte compartment containing a cathode separated by a divider, wherein the cathode comprises zinc, cadmium, tin, lead, copper or titanium or alloys thereof, mercury or mercury amalgam,
   (B) charging a solution containing said quaternary ammonium hydroxide which contains latent halide into the catholyte compartment,
   (C) charging an electrolyte to the anolyte compartment,
   (D) passing a current through the electrolytic cell to lower the latent halide content of the solution in the catholyte compartment, and
   (E) recovering the quaternary ammonium hydroxide solution from the catholyte compartment.

10. The process of claim 9 wherein the divider in the electrolytic cell is a gas separating membrane.

11. The process of claim 9 wherein the membrane in the electrolytic cell is a cation or anionic exchange membrane.

12. The process of claim 9 wherein the quaternary ammonium hydroxide in the solution charged to the catholyte in step (B) is characterized by the formula

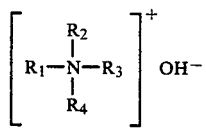

wherein $R_1$, $R_2$, $R_3$ and $R_4$ are each independently alkyl groups containing from one to about 10 carbon atoms, hydroxyalkyl or alkoxyalkyl groups containing from two to about 10 carbon atoms, aryl groups, or hydroxyaryl groups.

13. The process of claim 12 wherein $R_1$, $R_2$, $R_3$ and $R_4$ are each independently alkyl groups containing one to three carbon atoms or hydroxylalkyl groups containing two or three carbon atoms.

14. The process of claim 12 wherein $R_1$, $R_2$, $R_3$ and $R_4$ are methyl or ethyl groups.

15. The process of claim 9 wherein the quaternary ammonium hydroxide charged to the catholyte compartment in step (B) also contains ionic chloride.

16. The process of claim 9 wherein the electrolyte charged to the anolyte compartment in (C) is a solution of a quaternary ammonium hydroxide.

17. The process of claim 9 wherein the concentration of the quaternary ammonium hydroxide in the solution charged to the catholyte in step (B) is from about 3 to about 55% by weight.

18. The process of claim 9 wherein the cathode is a zinc or a zinc-alloy cathode.

19. A process for the electrolysis of an aqueous solution of quaternary ammonium hydroxide prepared by electrolyzing a quaternary ammonium halide salt in an electrolytic cell and which contains latent halide which comprises the steps of (A) providing an electrolytic cell comprising an anolyte compartment containing an anode and a catholyte compartment containing a cathode separated by an ion-exchange membrane, wherein the cathode comprises zinc, cadmium, tin, lead, copper or titanium or alloys thereof, mercury or mercury amalgam (B) charging an aqueous solution containing said quaternary ammonium hydroxide containing latent halide into the catholyte compartment, said quaternary ammonium hydroxide being characterized by the formula

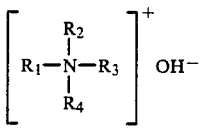

wherein $R_1$, $R_2$, $R_3$ and $R_4$ are each independently alkyl groups containing from one to about 10 carbon atoms, hydroxyalkyl or alkoxyalkyl groups containing from two to about 10 carbon atoms, (C) charging an aqueous electrolyte to the anolyte compartment, (D) passing a current through the electrolytic cell to lower the latent halide content of the solution in the catholyte compartment, and (E) recovering the quaternary ammonium hydroxide solution from the catholyte compartment.

20. The process of claim 19 wherein $R_1$, $R_2$, $R_3$ and $R_4$ are each independently alkyl groups containing one to three carbon atoms or hydroxyalkyl groups containing two or three carbon atoms.

21. The process of claim 20 wherein $R_1$, $R_2$, $R_3$ and $R_4$ are methyl or ethyl groups.

22. The process of claim 19 wherein the solution charged to the catholyte compartment in step (B) also contains ionic chloride.

23. The process of claim 19 wherein the electrolyte charged to the anolyte is an aqueous quaternary ammonium hydroxide solution.

24. A process of claim 19 wherein the concentration of the quaternary ammonium hydroxide in the aqueous solution charged to the catholyte in step (B) is from about 3 to about 55% by weight.

25. The process of claim 24 wherein the concentration is from about 5 to about 30% by weight.

26. The process of claim 19 wherein the quaternary ammonium hydroxide solution recovered in step (E) contains less than 5 ppm of latent halide.

27. The process of claim 19 wherein the cathode is a zinc or a zinc alloy cathode.

28. The process of claim 19 wherein the cathode is a zinc or a zinc-alloy cathode.

29. A process for the electrolysis of an aqueous solution of quaternary ammonium hydroxide prepared by electrolyzing a quaternary ammonium chloride salt in an electrolytic cell which contains latent chloride, the process comprising the steps of (A) providing an electrolytic cell comprising an anolyte compartment containing an anode and an electrolyte, and a catholyte compartment containing a zinc or zinc alloy cathode separated by a cation exchange membrane, (B) charging an aqueous solution containing a quaternary ammonium hydroxide containing latent chloride into the catholyte compartment, said quaternary ammonium hydroxide being characterized by the formula

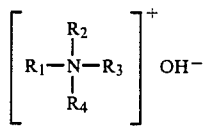

wherein $R_1$, $R_2$, $R_3$ and $R_4$ are each independently alkyl groups containing from one to about 10 carbon atoms or hydroxyalkyl groups containing from two to about 10 carbon atoms, (C) passing a direct current through the electrolytic cell for a period of time effective to convert at least some of the latent chloride in the solution in the catholyte to ionic chloride, and (D) recovering the quaternary ammonium hydroxide solution from the catholyte compartment, said quaternary ammonium hydroxide containing less than about 5 ppm of latent chloride.

30. The process of claim 29 wherein the concentration of quaternary ammonium hydroxide in the aqueous solution charged in step (B) is between about 5 to about 40% by weight.

31. The process of claim 29 wherein $R_1$, $R_2$, $R_3$ and $R_4$ are each methyl or ethyl groups or hydroxyethyl or hydroxypropyl groups.

32. The process of claim 29 wherein $R_1$, $R_2$, $R_3$ and $R_4$ are each methyl groups.

33. The process of claim 29 wherein the quaternary ammonium hydroxide recovered in step (D) contains less than 2 ppm of latent chloride.

34. The aqueous quaternary ammonium hydroxide solution obtained by the process of claim 29.

35. A process for the electrolysis of an aqueous solution of quaternary ammonium hydroxide prepared by electrolyzing a quaternary ammonium chloride salt in an electrolytic cell and which contains latent chloride, the process comprising the steps of
(A) providing an electrolytic cell comprising an anolyte compartment containing an anode and an electrolyte, and a catholyte compartment containing a zinc or zinc alloy cathode separated by an anion-exchange membrane,
(B) charging an aqueous solution containing a quaternary ammonium hydroxide containing latent chloride into the catholyte compartment, said quaternary ammonium hydroxide being characterized by the formula

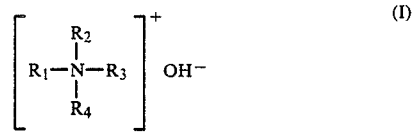

wherein $R_1$, $R_2$, $R_3$ and $R_4$ are each independently alkyl groups containing from one to about 10 carbon atoms or hydroxyalkyl groups containing from two to about 10 carbon atoms,
(C) passing a direct current through the electrolytic cell for a period of time effective to convert at least some of the latent chloride in the solution in the catholyte to ionic chloride, and
(D) recovering the quaternary ammonium hydroxide solution from the catholyte compartment, said quaternary ammonium hydroxide containing less than about 5 ppm of latent chloride.

36. The process of claim 35 wherein $R_1$, $R_2$, $R_3$ and $R_4$ are each methyl or ethyl groups or hydroxyethyl or hydroxypropyl groups.

* * * * *